(12) United States Patent
Lee

(10) Patent No.: US 10,022,209 B2
(45) Date of Patent: Jul. 17, 2018

(54) ELECTRIC TOOTHBRUSH

(71) Applicant: Bluereo Inc., Seoul (KR)

(72) Inventor: Seung Min Lee, Seoul (KR)

(73) Assignee: Bluereo Inc., Seoul (KR)

( * ) Notice: Subject to any disclaimer, the term of this patent is extended or adjusted under 35 U.S.C. 154(b) by 113 days.

(21) Appl. No.: 15/306,013

(22) PCT Filed: May 26, 2016

(86) PCT No.: PCT/KR2016/005552
§ 371 (c)(1),
(2) Date: Oct. 21, 2016

(87) PCT Pub. No.: WO2017/122883
PCT Pub. Date: Jul. 20, 2017

(65) Prior Publication Data
US 2018/0008388 A1 Jan. 11, 2018

(30) Foreign Application Priority Data
Jan. 13, 2016 (KR) ........................ 10-2016-0004324

(51) Int. Cl.
*A61C 17/34* (2006.01)
*A46B 13/02* (2006.01)
(Continued)

(52) U.S. Cl.
CPC ........ *A61C 17/3481* (2013.01); *A46B 13/023* (2013.01); *A61C 17/222* (2013.01);
(Continued)

(58) Field of Classification Search
CPC ....... A46B 13/023; A46B 13/04; A61C 17/22; A61C 17/222; A61C 17/225; A61C 17/32; A61C 17/34; A61C 17/3481; A61C 17/36
(Continued)

(56) References Cited

U.S. PATENT DOCUMENTS 8,793,829 B2 * 8/2014 Shimoyama ......... A46B 13/023
15/22.1
2002/0120991 A1 * 9/2002 Cacka .................. A61C 17/225
15/22.1
(Continued)

FOREIGN PATENT DOCUMENTS

JP 2011-200464 A 10/2011
JP 2012-183218 A 9/2012
(Continued)

*Primary Examiner* — Mark Spisich
(74) *Attorney, Agent, or Firm* — Novick, Kim & Lee, PLLC; Sang Ho Lee

(57) ABSTRACT

The present disclosure relates to an electric toothbrush, and more particularly, to an electric toothbrush including: a main body which includes an outer case; a cleaning body which is coupled to the main body and has a cleaning head formed at one end thereof; a vibration transmission unit which couples the main body and the cleaning body, has a vibration generator mounted thereon to generate vibration, and transmits the vibration to the cleaning body; and a vibration damping unit which is provided between the outer case and the vibration transmission unit, thereby maintaining cleaning performance of the electric toothbrush, reducing magnitude of vibration to be transmitted to a user, and improving convenience for the user.

11 Claims, 16 Drawing Sheets

(51) Int. Cl.
*A61C 17/22* (2006.01)
*A61C 17/36* (2006.01)
*A46B 13/04* (2006.01)

(52) U.S. Cl.
CPC ............ *A61C 17/225* (2013.01); *A61C 17/36* (2013.01); *A46B 13/04* (2013.01)

(58) Field of Classification Search
USPC .......................................................... 15/22.1
See application file for complete search history.

(56) References Cited

U.S. PATENT DOCUMENTS

| | | | |
|---|---|---|---|
| 2003/0162146 A1* | 8/2003 | Shortt ................... | A61C 17/34 433/118 |
| 2010/0199445 A1* | 8/2010 | Barman ................ | A61C 17/222 15/22.1 |
| 2010/0269275 A1* | 10/2010 | Shimoyama ....... | A61C 17/3481 15/22.1 |
| 2011/0010874 A1* | 1/2011 | Dickie ................. | A46B 5/0062 15/22.1 |

FOREIGN PATENT DOCUMENTS

| | | |
|---|---|---|
| KR | 10-2012-0076379 | 7/2012 |
| KR | 10-2012-0079167 A | 7/2012 |
| KR | 10-2013-0090502 A | 8/2013 |

\* cited by examiner

ELECTRIC TOOTHBRUSH

BACKGROUND

This application is prepared under the Research and Business Development program, which is funded by the Ministry of Trade, Industry and Energy (N002012), Republic of Korea.

Field

The present disclosure relates to an electric toothbrush, and more particularly, to an electric toothbrush which vibrates a head of the toothbrush by using electric power and cleans teeth.

Description of the Related Art

The most typical tool for cleaning teeth is a toothbrush, and the toothbrush is a tool used to clean the teeth with toothpaste attached to the toothbrush for the purpose of health care, hygiene, and cleanliness for the teeth. The toothbrush includes a main body formed in the form of a stick, and a brush formed by densely planting thin bristle members on a cleaning body formed at one end of the main body.

Typically, the toothbrush is used to remove foreign substances such as food particles or dental calculus stuck between the teeth, and a user grasps a handle portion of the toothbrush and moves a wrist or an arm, thereby removing foreign substances.

However, when the user brushes the teeth by directly moving the wrist or the arm as described above, the user is inconvenienced because the user needs to flex his/her wrist or arm, and the gum or the interior of the mouth is often injured because an effort to move the toothbrush is not uniform.

To solve the aforementioned problems, there has been proposed an electric toothbrush which has a vibration motor mounted in the toothbrush and vibrates the vibration motor by using electric power, thereby minimizing the movement of the user's wrist or arm, and improving convenience for the user through a brush vibrating by electric power.

However, a typical electric toothbrush in the related art has problems in that vibration of the vibration motor is transmitted as it is to the handle portion grasped by the user, and the user's hand vibrates, which may make the user displeased when the user uses the electric toothbrush for a long period of time, and may degrade accuracy of an operation of cleaning the teeth because of vibration of the user's hand.

Meanwhile, a method of reducing magnitude of vibration of the vibration motor may be considered to maintain accuracy of an operation of cleaning the teeth and solve the problem of vibration of the user's hand, but in this case, there are problems in that vibration of the brush is also reduced, and cleaning performance of the electric toothbrush deteriorates.

As literature in the related art, there is Korean Patent Application Laid-Open No. 10-2013-0090502 (entitled "Vibration Toothbrush, published on Aug. 14, 2013).

SUMMARY

The present disclosure has been made in an effort to solve the aforementioned problems, and to provide an electric toothbrush for maintaining cleaning performance of the electric toothbrush, reducing magnitude of vibration to be transmitted to a user, and improving convenience for the user.

According to an aspect of the present disclosure, there is provided an electric toothbrush including: a main body which includes an outer case; a vibration transmission unit which couples the main body and a cleaning body, has a vibration generator mounted thereon to generate vibration, and transmits the vibration to the cleaning body; and a vibration damping unit which is provided between the outer case and the vibration transmission unit.

In addition, the vibration generator according to the exemplary embodiment of the present disclosure may be a vibration motor, and a motor accommodating portion in which the vibration motor is mounted may be formed on the vibration transmission unit.

In addition, the vibration damping unit according to the exemplary embodiment of the present disclosure may be made of an elastic material.

In addition, the vibration transmission unit according to the exemplary embodiment of the present disclosure may have an insertion portion which protrudes to a predetermined height so as to be inserted into the cleaning body, and the vibration damping unit may be penetratively coupled to the insertion portion.

In addition, a first fastening protruding portion and a fastening guide portion, which correspond to each other, may be formed on the insertion portion and the vibration damping unit according to the exemplary embodiment of the present disclosure, respectively, such that during a process in which the insertion portion is penetratively coupled to the vibration damping unit, the first fastening protruding portion is guided along the fastening guide portion and then caught and fixed by an end of the fastening guide portion.

In addition, a coupling protruding portion, which protrudes inward, may be formed at one end of the outer case according to the exemplary embodiment of the present disclosure, and a coupling recess, which corresponds to the coupling protruding portion, may be formed at an upper end of the vibration damping unit, such that during a process in which the vibration transmission unit is coupled to the outer case, the coupling protruding portion is seated on the coupling recess.

In addition, the vibration transmission unit according to the exemplary embodiment of the present disclosure may be fixed as a first bracket and a second bracket, which constitute a bracket case, are coupled.

In addition, a fitting protruding portion, which protrudes outward, may be formed on the motor accommodating portion according to the exemplary embodiment of the present disclosure, and a fixing unit, which is coupled to the fitting protruding portion and fixes the vibration transmission unit, may be formed on the bracket case.

In addition, an opening portion, which penetrates inner and outer surfaces of the bracket case, may be formed in the bracket case according to the exemplary embodiment of the present disclosure, and the fixing unit may be positioned in the opening portion.

In addition, the fixing unit according to the exemplary embodiment of the present disclosure may include: a first extension portion is formed on the bracket case and extends in a direction toward the opening portion; a second extension portion which extends from an end of the first extension portion in a direction toward the fitting protruding portion; and a fitting groove portion which is formed in the second extension portion and opened in a direction toward the fitting protruding portion so as to be fitted with and coupled to the fitting protruding portion.

In addition, a gap portion, which is formed as the outer case and the cleaning body are spaced apart from each other, may be formed around an outer surface of the vibration transmission unit according to the exemplary embodiment of the present disclosure.

In addition, a removing portion, which is spaced apart from the motor accommodating portion, may be formed on an inner surface of the outer case according to the exemplary embodiment of the present disclosure.

In addition, a power source unit may be positioned below the motor accommodating portion according to the exemplary embodiment of the present disclosure, and a non-contact space portion may be formed between the motor accommodating portion and the power source unit.

According to the present disclosure, the vibration damping unit, which may absorb vibration, is provided between the outer case and the vibration transmission unit, and attenuates vibration which is generated in the vibration transmission unit and transmitted to the outer case which is a handle portion grasped by a user, and as a result, it is possible to improve convenience for the user without degrading performance of the toothbrush.

In addition, according to the present disclosure, the gap portion, which is formed as the outer case and the cleaning body are spaced apart from each other, is positioned around the outer surface of the vibration transmission unit, and as a result, it is possible to inhibit vibration transmitted to the cleaning body from being transmitted directly to the outer case instead of the vibration transmission unit.

In addition, according to the present disclosure, a removing portion, which is spaced apart from the motor accommodating portion, is formed on the inner surface of the outer case, and as a result, it is possible to inhibit vibration of the motor accommodating portion from being transmitted directly to the outer case.

In addition, according to the present disclosure, the power source unit for supplying electric power to the vibration motor mounted on the motor accommodating portion is positioned below the motor accommodating portion, and the non-contact space portion, which inhibits contact between the motor accommodating portion and the power source unit, is formed between the motor accommodating portion and the power source unit, and as a result, it is possible to inhibit vibration generated in the motor accommodating portion from being transmitted to the outer case past the power source unit and the bracket case.

BRIEF DESCRIPTION OF THE DRAWINGS

The above and other aspects, features and other advantages of the present disclosure will be more clearly understood from the following detailed description taken in conjunction with the accompanying drawings, in which.

DETAILED DESCRIPTION OF THE EMBODIMENT

Figure 1:
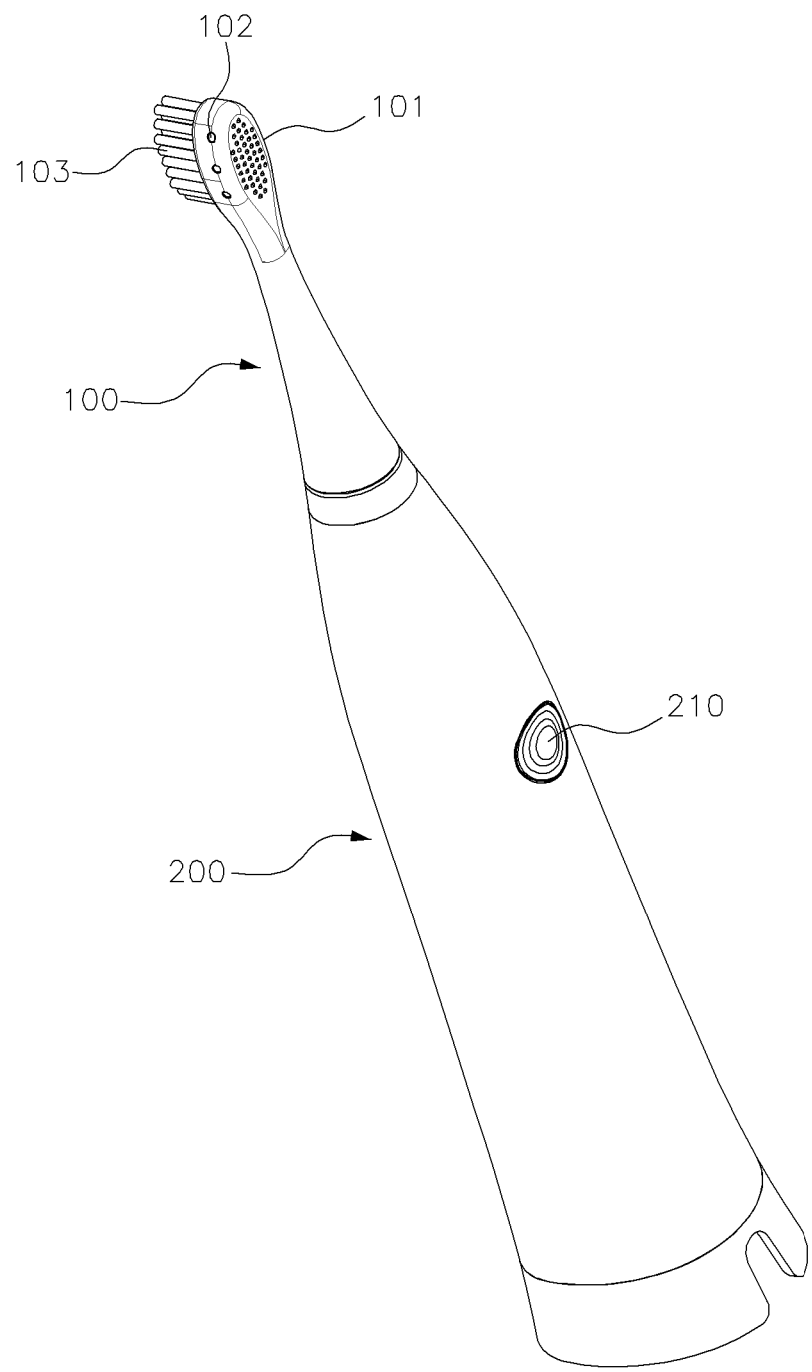
FIG. 1 is a perspective view of an electric toothbrush according to an exemplary embodiment of the present disclosure.

Advantages and features of the present disclosure and methods of achieving the advantages and features will be clear with reference to exemplary embodiments described in detail below together with the accompanying drawings.

However, the present disclosure is not limited to exemplary embodiment disclosed herein but will be implemented in various forms. The exemplary embodiments are provided so that the present disclosure is completely disclosed, and a person of ordinary skilled in the art can fully understand the scope of the present disclosure. Therefore, the present disclosure will be defined only by the scope of the appended claims. Like reference numerals indicate like elements throughout the specification.

Hereinafter, an exemplary embodiment of the present disclosure will be described in detail with reference to the accompanying drawings.

FIG. 1 is a perspective view of an electric toothbrush according to an exemplary embodiment of the present disclosure.

Referring to FIG. 1, the electric toothbrush according to the exemplary embodiment of the present disclosure has a structure that broadly includes a main body 200 and a cleaning body 100.

The main body 200 includes an outer case and defines a framework and an external shape of a lower portion of the tooth cleaning device, and is a handle portion substantially grasped by a user when the user uses the tooth cleaning device, and the cleaning body 100 is a portion used to clean teeth.

The cleaning body 100 may be separably coupled to the main body 200, a cleaning head 101 may be formed at one end of the cleaning body 100, and a brush 103 may be formed on the cleaning head 101 in one direction.

The brush 103 is used to brush the teeth, and configured such that a plurality of bristles is bundled, and the brush 103 may be separably coupled to the cleaning head 101 or formed integrally with the cleaning head 101.

The brush 103 may be coupled to the cleaning head 101 by a typical coupling method such as a threaded connection manner, or a press-fit manner, or by means of an assembling protrusion.

Nozzles 102 may be formed on an outer surface of the cleaning head 101, the nozzles 102 may be connected with a drive device that provides positive pressure or negative pressure through a flow path, and thus may spray a high-pressure washing liquid or suck gargling water in the mouth.

The nozzles 102 may be formed radially toward an outer circumferential surface of the cleaning head 101, and at least one nozzle 102 may be formed to improve efficiency in supplying the washing liquid or sucking the gargling water in the mouth, but the shape or the number of nozzles 102 is not limited.

An operating unit 210 may be provided on an outer circumferential surface of the main body 200, and the operating unit 210 may be a kind of a switch for operating a drive unit 270, and may perform a general operation on the tooth cleaning device such as an operation of manipulating a light emitting device, and an operation of generating vibration of the brush 103 by operating a vibration motor 240.

The operating unit 210 may be formed in the form of a button, but the present disclosure is not limited thereto, and the operating unit 210 may be formed to have a structure for implementing various operating manners such as a touch manner or a sliding manner.

Figure 2:
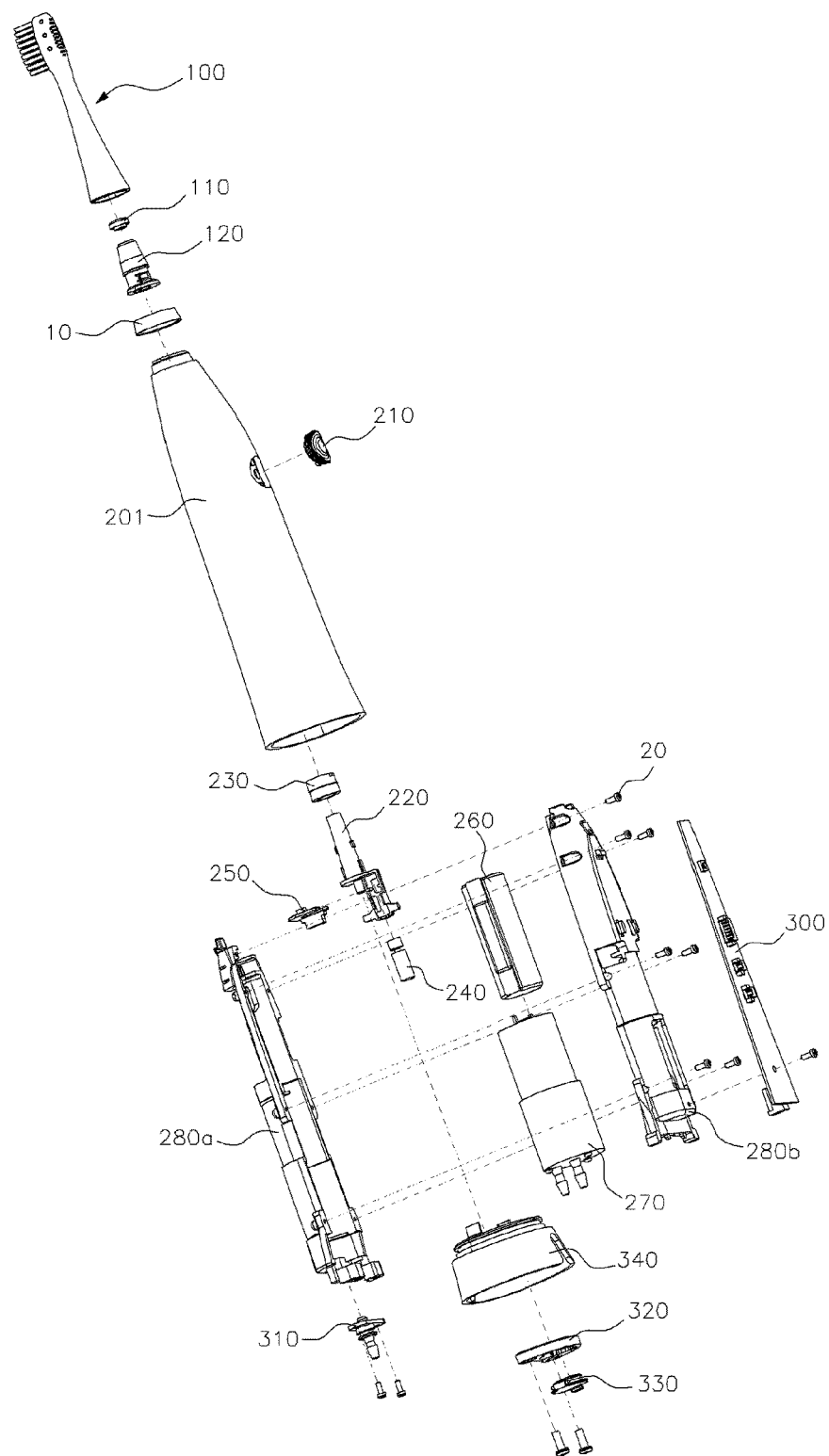
FIG. 2 is an exploded perspective view of the electric toothbrush according to the exemplary embodiment of the present disclosure.
Figure 3:
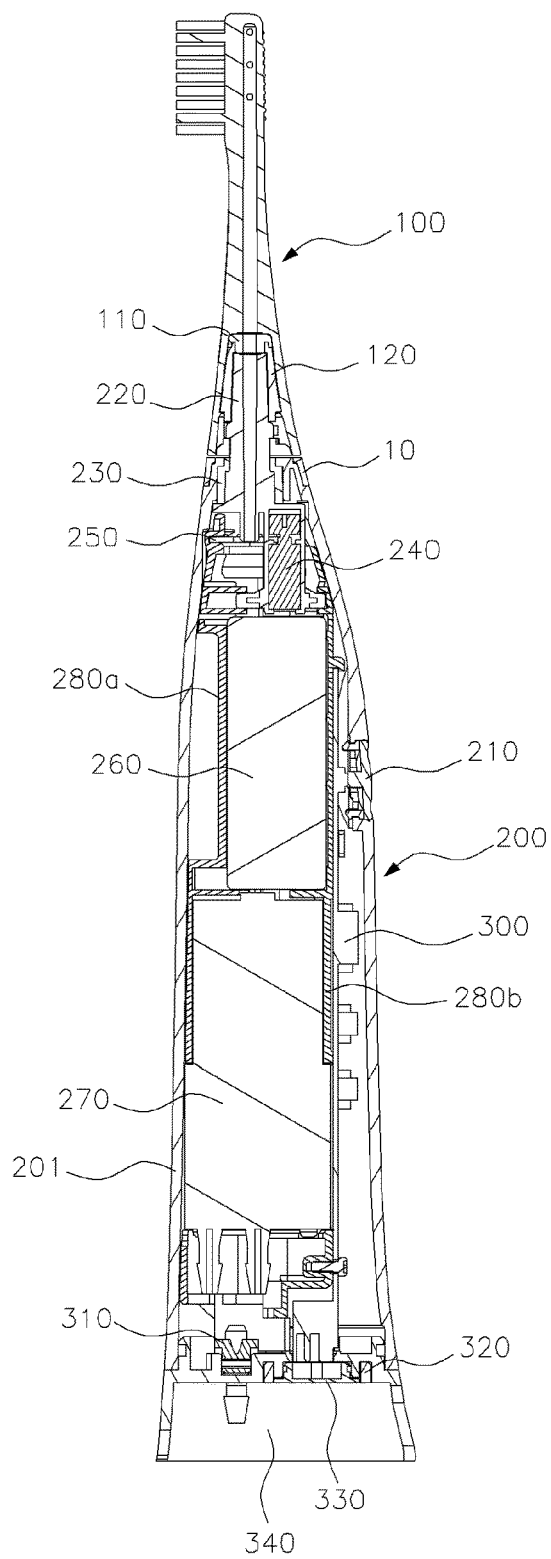
FIG. 3 is a cross-sectional view of the electric toothbrush according to the exemplary embodiment of the present disclosure.

FIG. 2 is an exploded perspective view of the electric toothbrush according to the exemplary embodiment of the present disclosure, and FIG. 3 is a cross-sectional view of the electric toothbrush according to the exemplary embodiment of the present disclosure.

Referring to FIGS. 2 and 3, the electric toothbrush according to the exemplary embodiment of the present disclosure includes the main body 200 and the cleaning body 100, and may include detailed constituent elements such as the drive unit 270 which supplies positive pressure for supplying a washing liquid or negative pressure for sucking gargling water, a vibration transmission unit 220 which couples the main body 200 and the cleaning body 100, a sealing unit 110 which is provided between the cleaning body 100 and the vibration transmission unit 220 and has a hollow space 111, a flange 120 which is separably coupled to an outer side of the vibration transmission unit 220 and inserted and fixed to the cleaning body 100, a light emitting unit 250 which emits light for brightening an interior of the mouth, the vibration motor 240 which provides vibration to the cleaning body 100, a power source unit 260 which supplies electric power, a control unit 300 which is connected with the operating unit 210 and controls the drive unit 270 or the light emitting unit 250, a first bracket 280a and a second bracket 280b which constitute a bracket case 281 that fixes components mounted in the main body 200, a nozzle unit 310 to which an O-ring is coupled, a DC cover unit 320 to which an O-ring is coupled, a DC cover guide unit 330 which guides a DC cover, a bottom case 340 which is mounted at a bottom of the main body 200, and screws 20 which are used to assemble the bracket.

For reference, the above drawings illustrate that the detailed constituent elements such as the drive unit 270 or the power source unit 260 are provided in the cleaning body 100, but these constituent elements may of course be positioned outside the cleaning body 100 as necessary, and because basic functions or structures of the respective constituent elements are widely known, detailed descriptions thereof will be omitted.

Figure 4:
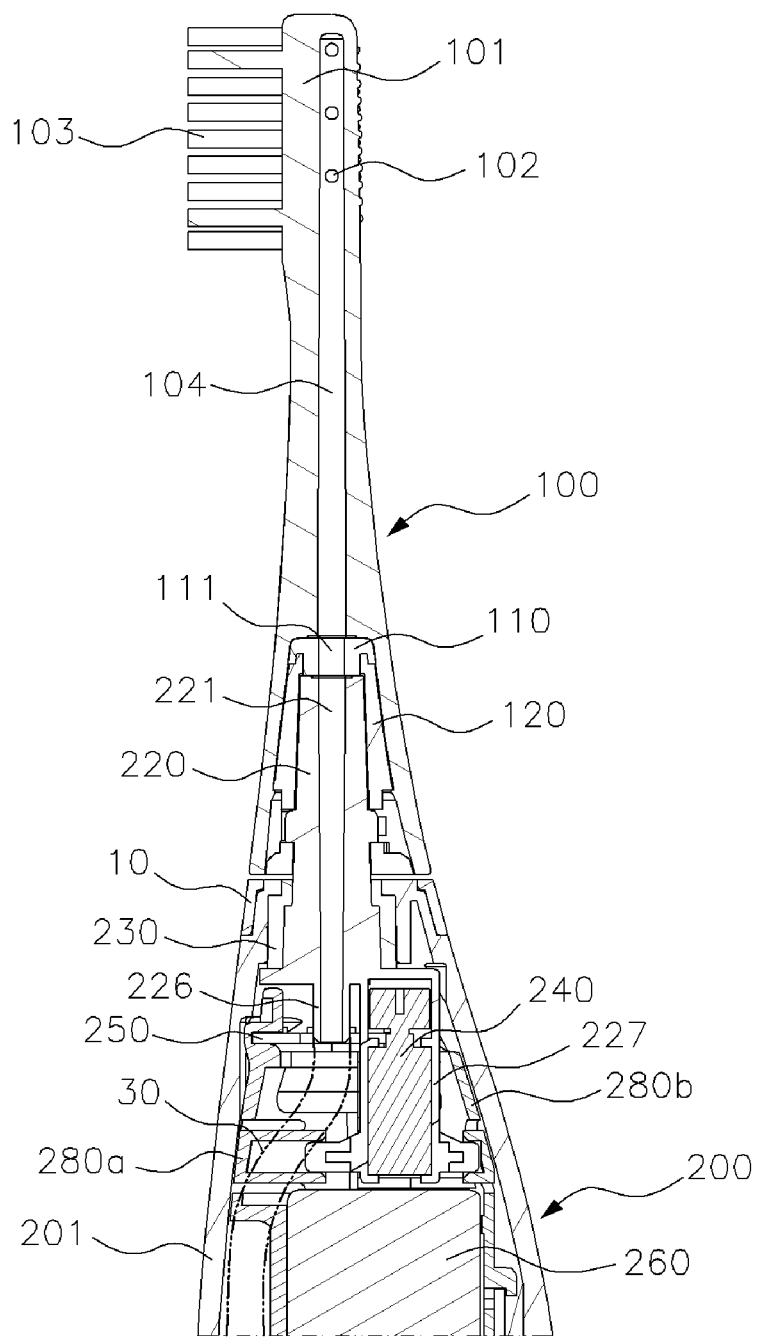
FIG. 4 is a partially cross-sectional view of the electric toothbrush according to the exemplary embodiment of the present disclosure.

FIG. 4 is a partially cross-sectional view of the electric toothbrush according to the exemplary embodiment of the present disclosure.

Referring to FIG. 4, the cleaning body 100 may be formed in a long bar shape, the cleaning head 101 to which the brush 103 is coupled is formed at one end of the cleaning body 100, and an internal fluid conduit 104, which extends in a longitudinal direction of the cleaning body 100 to a predetermined length, may be provided in the cleaning body 100.

The vibration transmission unit 220 couples the main body 200 and the cleaning body 100, and has a connecting flow path 221 formed therein, one side of the vibration transmission unit 220 may be coupled to the main body 200, and the other side of the vibration transmission unit 220 may be inserted into the cleaning body 100.

A motor accommodating portion 227 in which the vibration motor 240 is mounted may be formed in the vibration transmission unit 220, and a vibration generator for generating vibration is mounted to transmit vibration to the cleaning body 100, and when electric power is supplied to the vibration generator, the vibration generator generates vibration, and as a result, the vibration transmission unit 220 vibrates.

As the vibration transmission unit 220 vibrates, the cleaning body 100 coupled to the vibration transmission unit 220 vibrates, and the vibration is transmitted to the cleaning head 101 formed at one end of the cleaning body 100, and as a result, the brush 103 finally vibrates, thereby removing foreign substances on the teeth or in the mouth.

The drawings illustrate that the vibration generator is the vibration motor 240 and the motor accommodating portion 227 in which the vibration motor 240 is mounted is formed in the vibration transmission unit 220, but the present disclosure is not limited thereto, and all vibration generating devices, such as an actuator using an inductive coil, which are available in the technical field, may be included.

A tube extension portion 226 to which a replaceable connecting tube 30 may be coupled may be formed at one end of the vibration transmission unit 220.

Therefore, the internal fluid conduit 104 of the cleaning body 100, the hollow space 111 of the sealing unit 110, and the connecting flow path 221 of the vibration transmission unit 220 may be connected to each other to form a continuous flow path, and the continuous flow path may be further extended through the tube extension portion 226 of the vibration transmission unit 220 and the connecting tube 30 replaceably coupled to the tube extension portion 226, and may be extended to a connecting tube 30 for suction and a connecting tube 30 for discharge past the drive unit 270.

Figure 5:
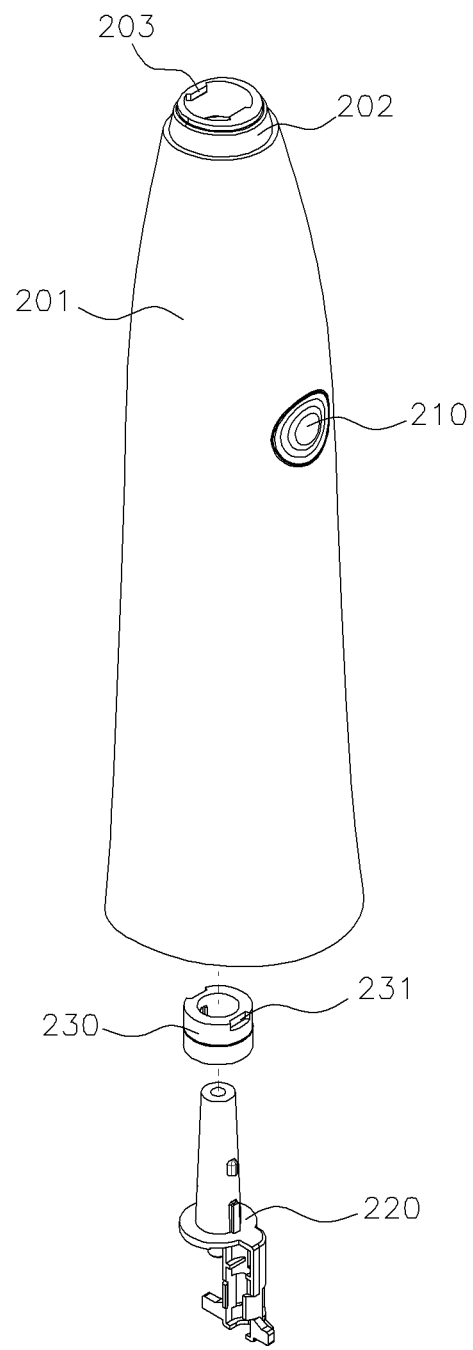
FIG. 5 is an exploded perspective view illustrating constituent elements including a vibration reducing unit of the electric toothbrush according to the exemplary embodiment of the present disclosure.
Figure 6A:
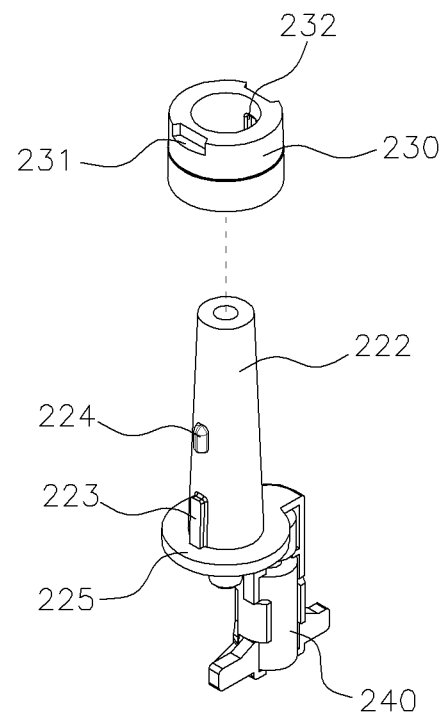
FIG. 6A is an exploded perspective view illustrating a vibration transmission unit and the vibration reducing unit according to the exemplary embodiment of the present disclosure.
Figure 6B:
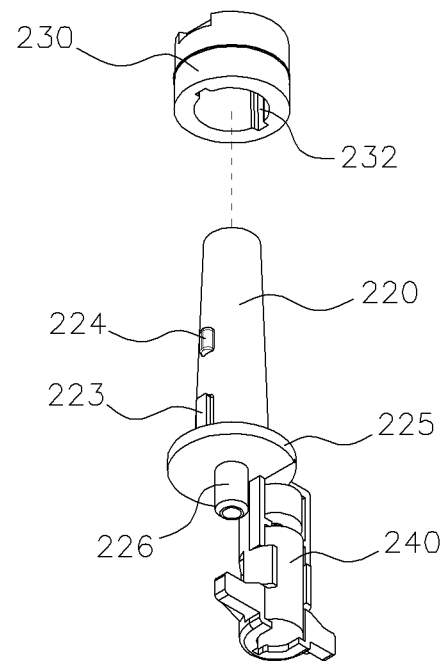
FIG. 6B is a view illustrating the exploded perspective view of FIG. 6A at a different angle.

FIG. 5 is an exploded perspective view illustrating constituent elements including a vibration reducing unit of the electric toothbrush according to the exemplary embodiment of the present disclosure, FIG. 6A is an exploded perspective view illustrating the vibration transmission unit and the vibration reducing unit according to the exemplary embodiment of the present disclosure, and FIG. 6B is a view illustrating the exploded perspective view of FIG. 6A at a different angle.

Referring to FIGS. 5, 6A and 6B, a vibration damping unit 230, which has a hollow shape 111 having a vacant interior may be provided between the outer case 201 and the vibration transmission unit 220.

The vibration damping unit 230 may have a function of absorbing vibration, and therefore, the vibration, which is generated in the vibration transmission unit 220, is inhibited from being transmitted to the outer case 201 which is a handle portion grasped by the user, and as a result, it is possible to further improve convenience for the user without degrading toothbrush performance.

The vibration damping unit 230 may be made of an elastic material in order to maximize the vibration damping performance, and more particularly, the vibration damping unit 230 may be made of, but not limited to, silicone or a rubber-based elastic material.

Meanwhile, an insertion portion 222, which protrudes to a predetermined height so as to be inserted into the cleaning body 100, may be formed on the vibration transmission unit 220, and the vibration damping unit 230 may be penetratively coupled to an inner circumferential surface of the insertion portion 222.

A plate portion 225, which is formed in an approximately circular plate shape, may be formed at one end of the insertion portion 222, and the tube extension portion 226, which is positioned in the main body 200 and to which the replaceable connecting tube 30 may be coupled, may be formed on a lower surface of the plate portion 225.

First fastening protruding portions 223, which have a predetermined height and a predetermined length, may be formed on an outer surface of the insertion portion 222, and fastening guide portions 232, which correspond to the first fastening protruding portions 223, may be formed on an inner surface of the vibration damping unit 230, and as a result, the first fastening protruding portions 223 are guided along the fastening guide portions 232 and then caught and fixed by ends of the fastening guide portions 232 during the process in which the insertion portion 222 is penetratively fixed to the vibration damping unit 230.

The first fastening protruding portion 223 and the fastening guide portion 232 may have the same length, and in this case, the vibration damping unit 230 and the plate portion 225 of the vibration transmission unit 220 come into contact with each other in a state in which the vibration damping unit 230 and the vibration transmission unit 220 are not spaced apart from each other, and as a result, it is possible to further improve vibration damping performance.

Second fastening protruding portions 224 to be described below may be formed on the outer surface of the insertion portion 222, and the second fastening protruding portion 224 may be formed to be spaced upward apart from the first fastening protruding portion 223 at a predetermined interval, and may have a protruding height smaller than that of the first fastening protruding portion 223 so that the second fastening protruding portion 224 may pass over the fastening guide portion 232 without being caught by the fastening guide portion 232.

Coupling protruding portions 203, which protrude inward, are formed at one end of the outer case 201, and coupling recesses 231, which correspond to the coupling protruding portions 203, are formed at an upper end of the vibration damping unit 230, and as a result, the coupling protruding portions 203 may be seated on the coupling recesses 231 during the process in which the vibration transmission unit 220 is coupled to the outer case 201.

A plurality of coupling protruding portions 203 may be formed in a direction in which the plurality of coupling protruding portions 203 face each other, and the coupling recesses 231 may be formed such that the number and the positions of the coupling recesses 231 correspond to those of the coupling protruding portions 203. The coupling recess 231 is formed in an upper surface of the vibration damping unit 230 so as to have a predetermined size and correspond to the size of the coupling protruding portion 203, and as a result, a separation space between the outer case 201 and the vibration transmission unit 220 may be minimized.

Figure 7:
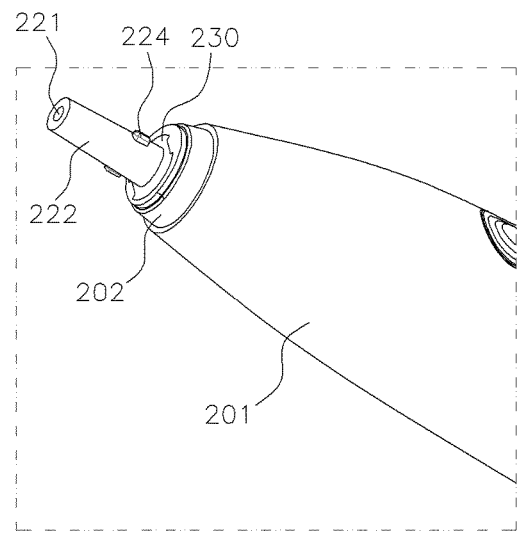
FIG. 7 is a coupled perspective view illustrating a result of assembling the constituent elements illustrated in the exploded perspective view of FIG. 5.

FIG. 7 is a coupled perspective view illustrating a result of assembling the constituent elements illustrated in the exploded perspective view of FIG. 5.

Referring to FIG. 7, the insertion portion 222 of the vibration transmission unit 220 and the second fastening protruding portion 224 formed on the outer circumferential surface of the insertion portion 222 are exposed to the outside of the outer case 201, and the vibration damping unit 230 is formed between the outer case 201 and the vibration transmission unit 220 so as to be able to absorb vibration generated in the vibration transmission unit 220. A groove portion 202 on which a decorative ring 10 is mounted may be formed at one end of the outer case 201.

Figure 8:
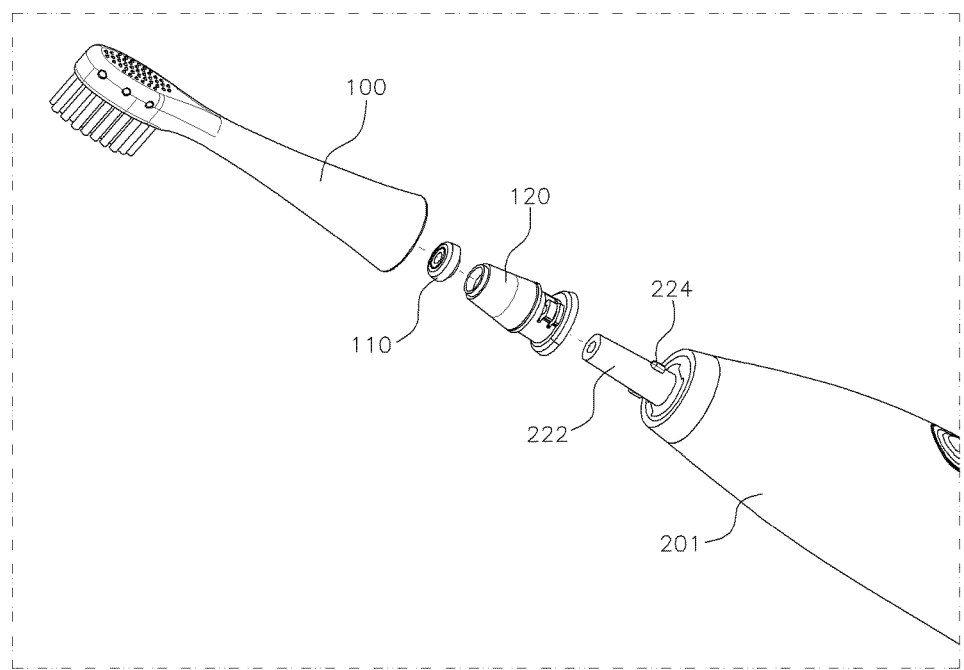
FIG. 8 is an exploded perspective view illustrating constituent elements including the vibration transmission unit and a cleaning body according to the exemplary embodiment of the present disclosure.

FIG. 8 is an exploded perspective view illustrating constituent elements including the vibration transmission unit and the cleaning body according to the exemplary embodiment of the present disclosure.

Referring to FIG. 8, the second fastening protruding portions 224 are formed along the outer surface of the insertion portion 222, and coupling channels are formed in an inner surface of the flange 120, and as a result, the second fastening protruding portion 224 is guided along the coupling channel and then caught and fixed by one side of the coupling channel during the process in which the insertion portion 222 is coupled to the flange 120, such that the vibration transmission unit 220 and the flange 120 may be coupled to each other.

In this case, the vibration transmission unit 220 may transmit vibration to the cleaning body 100 through the flange 120 or the sealing unit 110, and the paths through which the vibration is transmitted from the vibration transmission unit 220 to the cleaning body 100 may be changed depending on the structures of or the coupling relationships between the respective constituent elements, but the present disclosure is not limited thereto.

Figure 9:
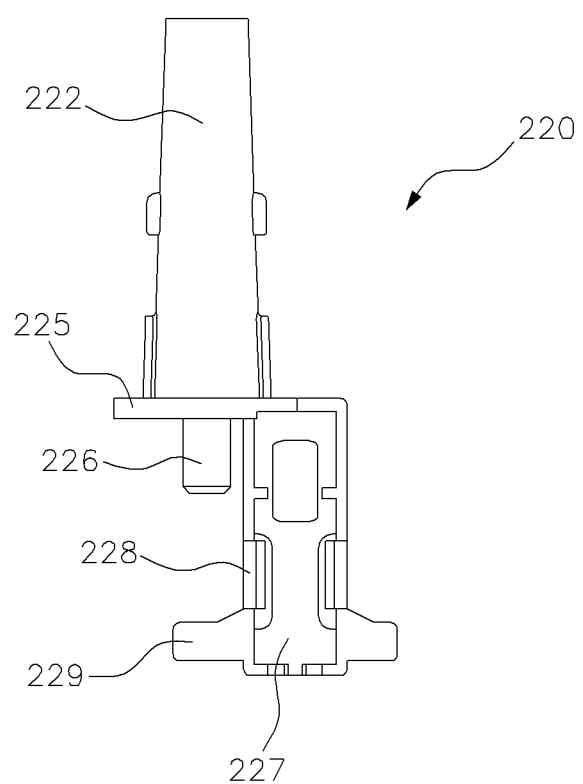
FIG. 9 is a view illustrating the vibration transmission unit according to the exemplary embodiment of the present disclosure.
Figure 10:
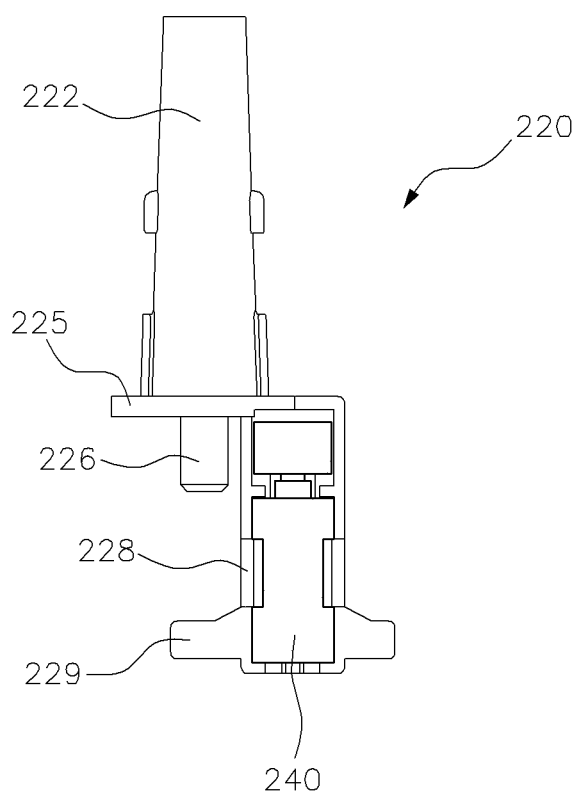
FIG. 10 is a view illustrating the vibration transmission unit mounted with a vibration motor according to the exemplary embodiment of the present disclosure.

FIG. 9 is a view illustrating the vibration transmission unit according to the exemplary embodiment of the present disclosure, and FIG. 10 is a view illustrating the vibration transmission unit mounted with the vibration motor according to the exemplary embodiment of the present disclosure.

Referring to FIGS. 9 and 10, the vibration transmission unit 220 according to the exemplary embodiment of the present disclosure may have the motor accommodating portion 227 in which the vibration motor 240 is mounted, the motor accommodating portion 227 may be formed to be opened at one side so that the vibration motor 240 may be inserted and mounted, and the motor accommodating portion 227 may be formed to correspond to the shape of the vibration motor 240 so that the vibration motor 240 may be seated.

Specifically, the motor accommodating portion 227 may have a shape formed by cutting in half a cylindrical shape having a length larger than a diameter in a longitudinal direction, and fixing protruding portions 228, which are formed to surround a part of an outer circumferential surface of the vibration motor 240, may be provided to fix the inserted vibration motor 240.

The fixing protruding portions 228 may be formed to have an appropriate length in an appropriate direction so as to easily assemble the vibration motor 240 and fix the vibration motor 240 against vibration of the vibration motor 240 after assembling the vibration motor 240.

Fitting protruding portions 229, which protrude outward and have a predetermined length, may be formed on the motor accommodating portion 227, and two fitting protruding portions 229 may extend from both surfaces of the motor accommodating portion 227 in the opposite directions.

Figure 11:
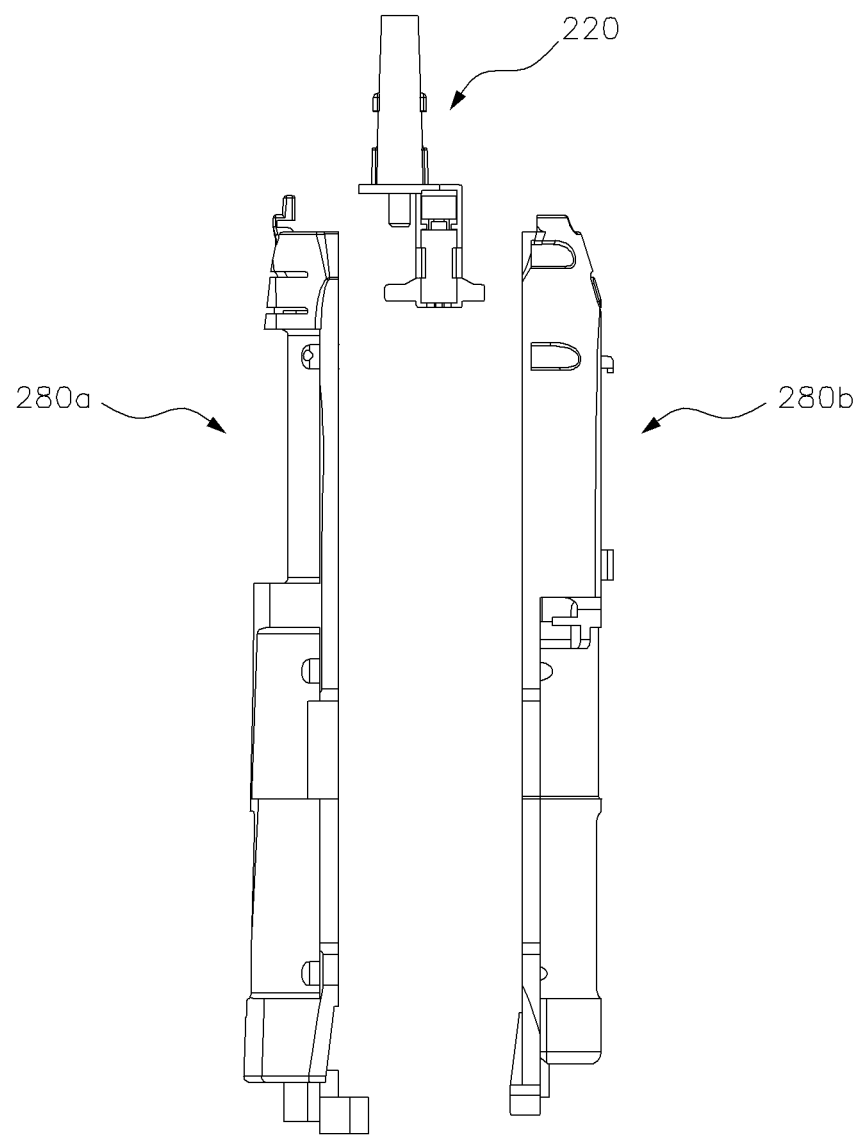
FIG. 11 is an exploded front view illustrating the vibration transmission unit and brackets according to the exemplary embodiment of the present disclosure.
Figure 12A:
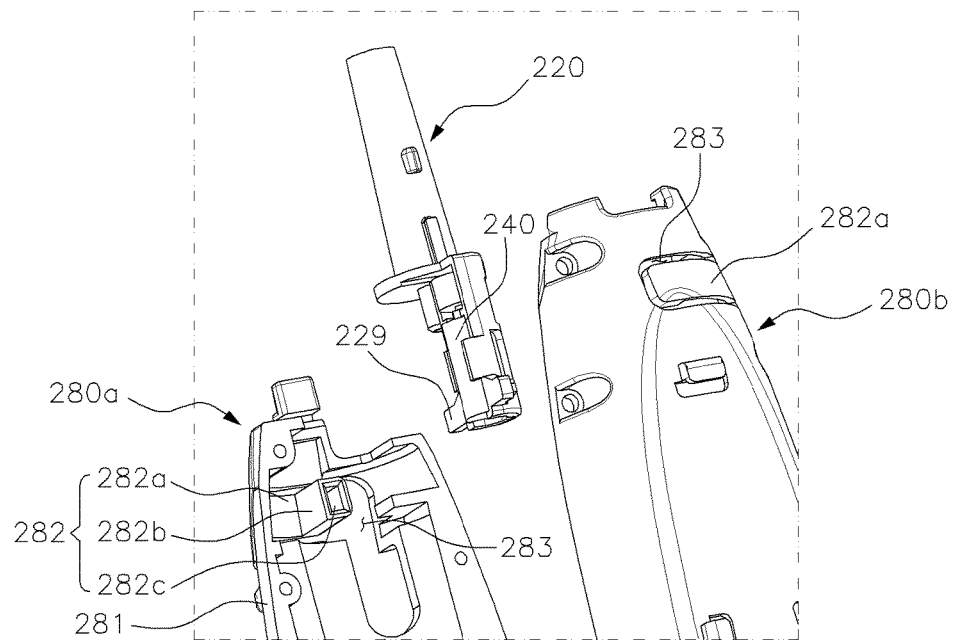
FIG. 12A is an exploded perspective view illustrating the vibration transmission unit and the brackets according to the exemplary embodiment of the present disclosure.
Figure 12B:
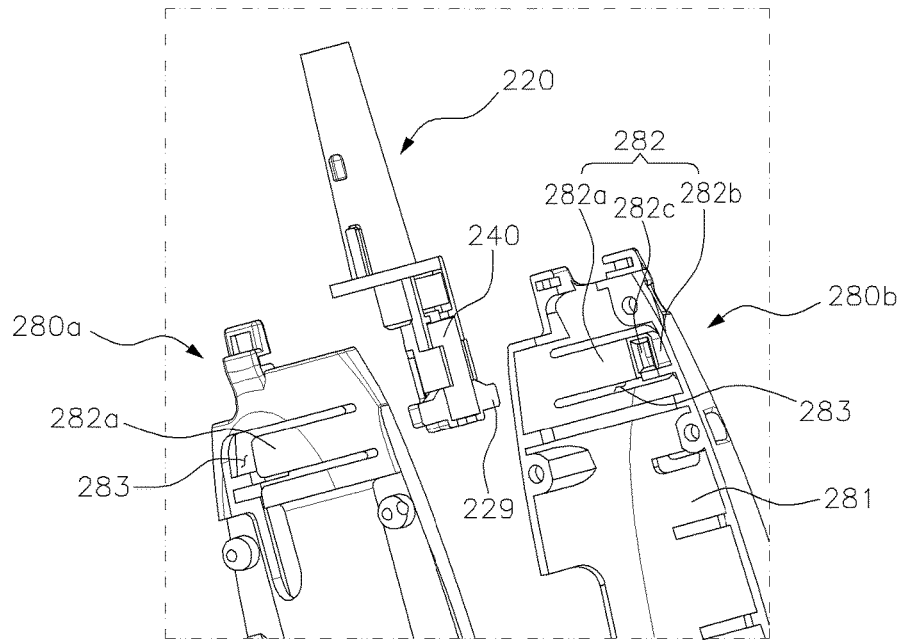
FIG. 12B is a view illustrating the exploded perspective view of FIG. 12A at a different angle.

FIG. 11 is an exploded front view illustrating the vibration transmission unit and brackets according to the exemplary embodiment of the present disclosure, FIG. 12A is an exploded perspective view illustrating the vibration transmission unit and the brackets according to the exemplary embodiment of the present disclosure, and FIG. 12B is a view illustrating the exploded perspective view of FIG. 12A at a different angle.

Referring to FIGS. 11, 12A and 12B, the fitting protruding portions 229, which protrude outward, are formed on the motor accommodating portion 227 of the vibration transmission unit 220 as described above, and fixing units 282, which are coupled to the fitting protruding portions 229 and fix the vibration transmission unit 220, may be formed in the bracket case 281, and the vibration transmission unit 220 may be fixed to the main body 200 as the first bracket 280a and the second bracket 280b, which constitute the bracket case 281, are coupled to each other.

Opening portions 283, which penetrate inner and outer surfaces of the bracket case 281, may be formed in the bracket case 281, the fixing units 282 are positioned in the opening portions 283, and the opening portions 283 may be formed in the bracket case 281 so as to have a predetermined size, and may be formed at positions where the fixing units 282 for fixing the vibration transmission unit 220 are suitably formed.

Specifically, the fixing unit 282 may include a first extension portion 282a which extends in a direction toward the opening portion 283 from the bracket case 281, a second extension portion 282b which extends in a direction toward the fitting protruding portion 229 of the vibration transmission unit 220 from an end of the first extension portion 282a, and a fitting groove portion 282c which is formed in the second extension portion 282b and opened in a direction toward the fitting protruding portion 229 so that the fitting protruding portion 229 is fitted into the fitting groove portion 282c.

Figure 13:
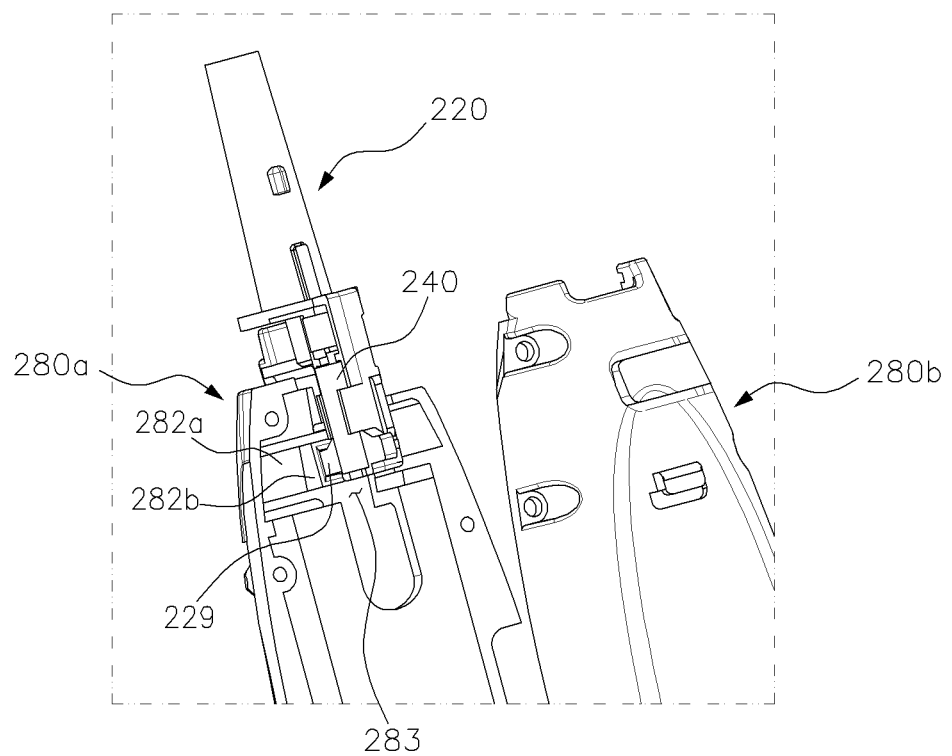
FIG. 13 is a coupled perspective view illustrating a result of assembling the vibration transmission unit and a first bracket according to the exemplary embodiment of the present disclosure.
Figure 14:
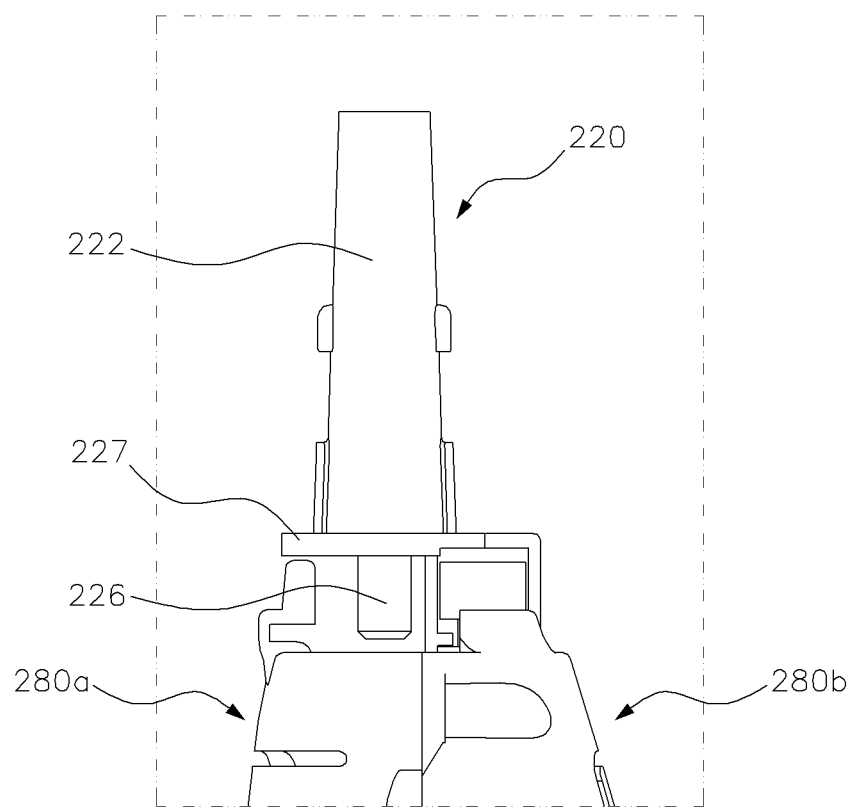
FIG. 14 is a view illustrating a result of assembling the vibration transmission unit, the first bracket, and a second bracket according to the exemplary embodiment of the present disclosure.

FIG. 13 is a coupled perspective view illustrating a result of assembling the vibration transmission unit and the first bracket according to the exemplary embodiment of the present disclosure, and FIG. 14 is a view illustrating a result of assembling the vibration transmission unit, the first bracket, and the second bracket according to the exemplary embodiment of the present disclosure.

Referring to FIGS. 13 and 14, the fitting protruding portion 229 of the vibration transmission unit 220 according to the exemplary embodiment of the present disclosure is fitted into and coupled to the fitting groove portion 282c formed in the second extension portion 282b of the fixing unit 282.

Therefore, when the vibration motor 240 vibrates by being supplied with electric power, the motor accommodating portion 227 and the fitting protruding portions 229 formed on the motor accommodating portion 227 vibrate together, and the fixing units 282 coupled to the fitting protruding portions 229 vibrate in a direction toward the outside and the inside of the opening portions 283.

Specifically, when the vibration motor 240 vibrates, the first extension portion 282a and the second extension portion 282b perform rotational motion within a predetermined angle based on a portion where the bracket case 281 and the fixing unit 282 about each other, and the vibration generated by the vibration motor 240 is not immediately transmitted to the entirety of the bracket case 281, but transmitted first to the fixing unit 282 positioned in the opening portion 283.

Because of the opening portion 283 formed in the bracket case 281, the fixing unit 282 has elasticity so as to be movable in the direction toward the inside and the outside of the bracket case 281, and as a result, it is possible to primarily attenuate vibration transmitted from the motor accommodating portion 227, and to greatly attenuate vibration transmitted to the outer case 201 coupled to the bracket case 281.

Figure 15:
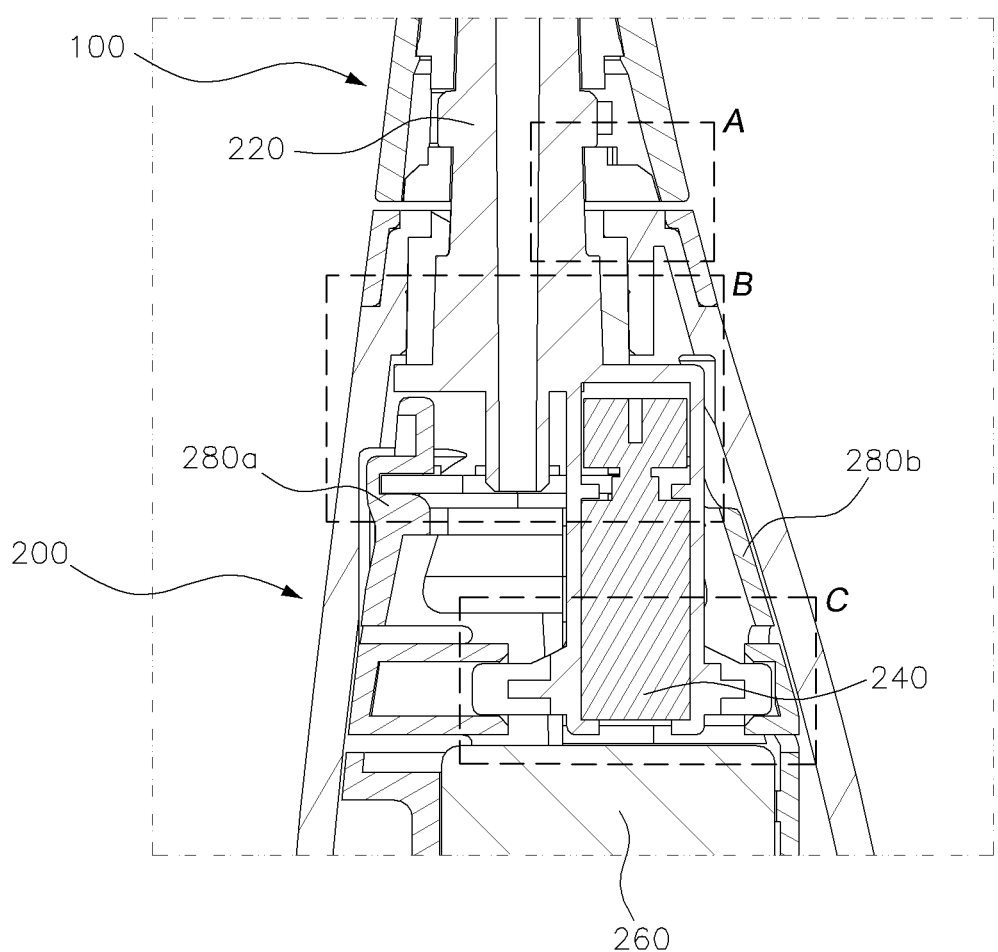
FIG. 15 is a partially cross-sectional view of the electric toothbrush for showing vibration damping performance according to the exemplary embodiment of the present disclosure.
Figure 16A:
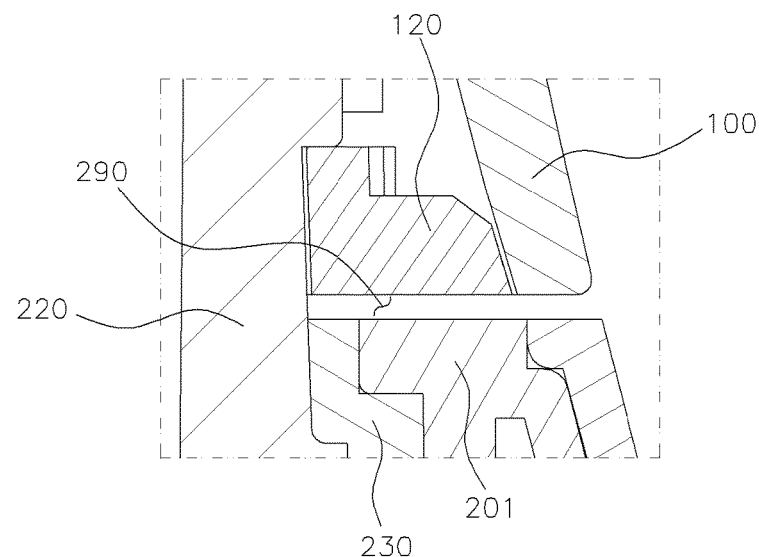
FIG. 16A is an enlarged view of part A in FIG. 15.
Figure 16B:
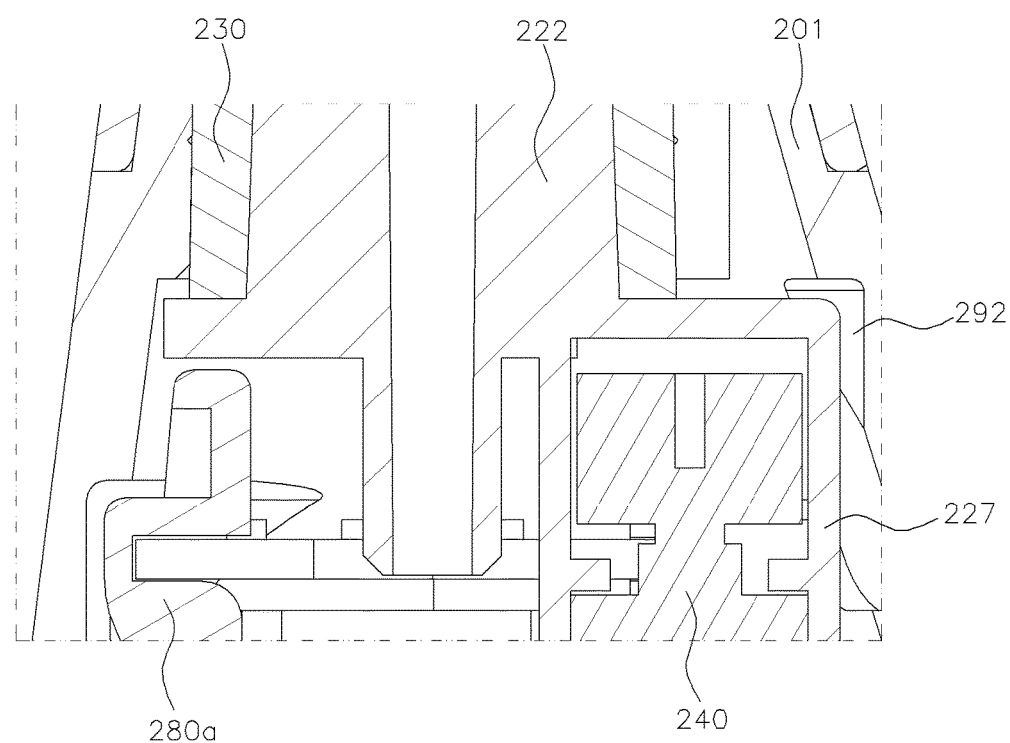
FIG. 16B is an enlarged view of part B in FIG. 15.
Figure 16C:
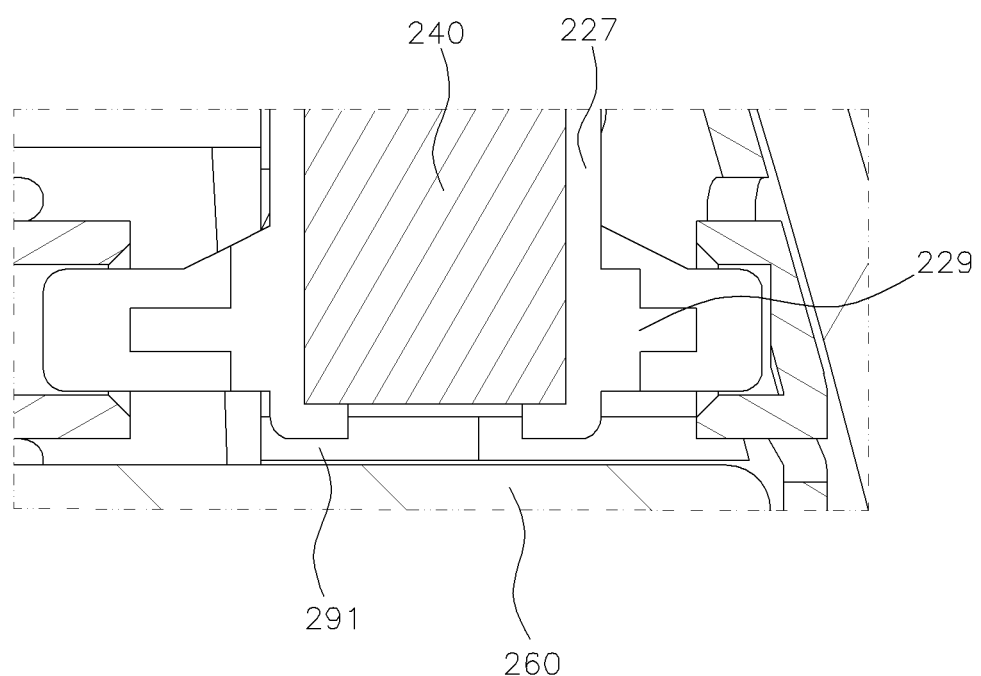
FIG. 16C is an enlarged view of part C in FIG. 15.

FIG. 15 is a partially cross-sectional view of the electric toothbrush for showing vibration damping performance according to the exemplary embodiment of the present disclosure, FIG. 16A is an enlarged view of part A in FIG. 15, FIG. 16B is an enlarged view of part B in FIG. 15, and FIG. 16C is an enlarged view of part C in FIG. 15.

Referring to FIGS. 15 and 16A, a gap portion 290, which is formed as the outer case 201 and the cleaning body 100 are spaced apart from each other, may be positioned around the outer surface of the vibration transmission unit 220 according to the exemplary embodiment of the present disclosure. Therefore, it is possible to inhibit the vibration transmitted to the cleaning body 100 from being transmitted directly to the outer case 201 instead of the vibration transmission unit 220.

In this case, if a size of the gap portion 290 is excessively large, the vibration transmission unit 220 is exposed to the outside, which causes a problem of a poor aesthetic appearance, and if a size of the gap portion 290 is excessively small, there may occur a problem in that the cleaning body 100 comes into contact with the outer case 201 when the cleaning body 100 vibrates, and vibration is partially transmitted directly to the outer case 201, and as a result, the gap portion 290 needs to have an appropriate size.

Referring to FIGS. 15 and 16B, a removing portion 292, which is spaced apart from the motor accommodating portion 227, may be formed on an inner surface of the outer case 201 according to the exemplary embodiment of the present disclosure.

The connecting flow path 221 is formed in the vibration transmission unit 220, the tube extension portion 226 is formed at one end of the vibration transmission unit 220, and the replaceable connecting tube 30 may be connected to the tube extension portion 226, and in a case in which the connecting flow path 221 and the tube extension portion 226 define a central axis of the vibration transmission unit 220, the central axis of the vibration transmission unit 220 is eccentric with respect to a central axis of the motor accommodating portion 227 formed on the vibration transmission unit 220.

The motor accommodating portion 227 may come into contact with the outer case 201, and since the removing portion 292, which is spaced apart from the motor accommodating portion 227, is formed on the inner surface of the outer case 201 at the position where the motor accommodating portion 227 is eccentrically disposed and may come into contact with the outer case 201, it is possible to inhibit vibration of the motor accommodating portion 227 from being transmitted directly to the outer case 201.

Referring to FIGS. 15 and 16C, the power source unit 260 is positioned below the motor accommodating portion 227 according to the exemplary embodiment of the present disclosure, and a non-contact space portion 291 may be formed between the motor accommodating portion 227 and the power source unit 260.

The power source unit 260 for supplying electric power to the vibration motor 240 mounted in the motor accommodating portion 227 may be positioned below the motor accommodating portion 227, and the non-contact space portion 291, which inhibits contact between the motor accommodating portion 227 and the power source unit 260, is formed between the motor accommodating portion 227 and the power source unit 260, and as a result, it is possible to inhibit vibration generated in the motor accommodating portion 227 from being transmitted to the outer case 201 past the power source unit 260 and the bracket case 281.

As the foregoing, all of the constituent elements, which constitute the exemplary embodiment according to the present disclosure, have been described as being integrally coupled or operated after being coupled, but the present disclosure is not necessarily limited to the exemplary embodiment. That is, within the scope of the object of the present disclosure, one or more of all of the constituent elements can be selectively coupled and operated. In addition, unless explicitly described to the contrary, the term "comprising", "including", or "having" will be understood to imply the inclusion of stated constituent elements but not the exclusion of any other constituent elements. All terms used herein including technical or scientific terms have the same meanings as meanings which are generally understood by those skilled in the art unless they are differently defined. Terms defined in generally used dictionary shall be construed that they have meanings matching those in the context of the related art, and shall not be construed in ideal or excessively formal meanings unless they are clearly defined in the present disclosure.

What is claimed is:

1. An electric toothbrush comprising:
a main body which includes an outer case;
a cleaning body which is coupled to the main body and has a cleaning head formed at one end thereof;
a vibration transmission unit which couples the main body and the cleaning body, has a vibration generator mounted thereon to generate vibration, and transmits the vibration to the cleaning body; and
a vibration damping unit which is provided between the outer case and the vibration transmission unit,
wherein a motor accommodating portion is formed in the vibration transmission unit, the vibration transmission unit is fixed to a bracket case, a fitting protruding portion, which protrudes outward, is formed on the motor accommodating portion, a fixing unit, which is coupled to the fitting protruding portion and fixes the vibration transmission unit, is formed on the bracket case, an opening portion, which penetrates inner and outer surfaces of the bracket case, is formed in the bracket case, and the fixing unit is positioned in the opening portion.

2. The electric toothbrush of claim 1, wherein the vibration generator is a vibration motor, and the motor accommodating portion in which the vibration motor is mounted is formed on the vibration transmission unit.

3. The electric toothbrush of claim 1, wherein the vibration damping unit is made of an elastic material.

4. The electric toothbrush of claim 1, wherein the vibration transmission unit has an insertion portion which protrudes to a predetermined height so as to be inserted into the cleaning body, and the vibration damping unit is penetratively coupled to the insertion portion.

5. The electric toothbrush of claim 4, wherein a first fastening protruding portion and a fastening guide portion, which correspond to each other, are formed on the insertion portion and the vibration damping unit, respectively, such that during a process in which the insertion portion is penetratively coupled to the vibration damping unit, the first fastening protruding portion is guided along the fastening guide portion and then caught and fixed by an end of the fastening guide portion.

6. The electric toothbrush of claim 4, wherein a coupling protruding portion, which protrudes inward, is formed at one end of the outer case, and a coupling recess, which corresponds to the coupling protruding portion, is formed at an upper end of the vibration damping unit, such that during a process in which the vibration transmission unit is coupled to the outer case, the coupling protruding portion is seated on the coupling recess.

7. The electric toothbrush of claim 1, wherein the vibration transmission unit is fixed as a first bracket and a second bracket, which constitute the bracket case, are coupled.

8. The electric toothbrush of claim 7, wherein a gap portion, which is formed as the outer case and the cleaning body are spaced apart from each other, is formed around an outer surface of the vibration transmission unit.

9. The electric toothbrush of claim 7, wherein a removing portion, which is spaced apart from the motor accommodating portion, is formed on an inner surface of the bracket case.

10. The electric toothbrush of claim 7, wherein a power source unit is positioned below the motor accommodating portion, and a non-contact space portion is formed between the motor accommodating portion and the power source unit.

11. The electric toothbrush of claim 1, wherein the fixing unit includes:
a first extension portion which extends from the bracket case in a direction toward the opening portion;
a second extension portion which extends from an end of the first extension portion in a direction toward the fitting protruding portion; and
a fitting groove portion which is formed in the second extension portion and opened in a direction toward the fitting protruding portion so as to be fitted with and coupled to the fitting protruding portion.

* * * * *